United States Patent [19]

Upson et al.

[11] Patent Number: 5,244,670
[45] Date of Patent: Sep. 14, 1993

[54] INGESTIBLE PHARMACEUTICAL COMPOSITIONS FOR TREATING UPPER GASTROINTESTINAL TRACT DISTRESS

[75] Inventors: James G. Upson, Springdale; Carmelita M. Russell, Cincinnati, both of Ohio

[73] Assignee: The Procter & Gamble Company, Cincinnati, Ohio

[21] Appl. No.: 887,128

[22] Filed: May 20, 1992

Related U.S. Application Data

[63] Continuation of Ser. No. 680,459, Apr. 4, 1991, abandoned.

[51] Int. Cl.$^5$ .................................................. A61K 9/28
[52] U.S. Cl. ..................................... 424/439; 424/441; 514/819; 514/820; 514/715
[58] Field of Search .......................................... 424/439

[56] References Cited

U.S. PATENT DOCUMENTS

| | | | |
|---|---|---|---|
| 3,991,178 | 11/1976 | Humbert et al. | 424/54 |
| 4,136,163 | 1/1979 | Watson et al. | 424/54 |
| 4,163,777 | 8/1979 | Mitra | 424/468 |
| 4,446,135 | 5/1984 | Fountaine | 424/441 |
| 4,459,425 | 7/1984 | Amano et al. | 568/666 |
| 4,486,412 | 12/1984 | Shah | 424/456 |
| 5,068,109 | 11/1991 | Foldager et al. | 424/441 |

FOREIGN PATENT DOCUMENTS 310299 4/1989 European Pat. Off. .

OTHER PUBLICATIONS

Physicians' Desk Reference For Nonprescription Drugs, 13th Edition (published by Medical Economics Company, Inc.; 1992) "Maalox" products at pp. 649-651; Tums products at pp. 720-721; and Rolaids products at pp. 757-758.

Jabloner et al., "A Molecular Approach to Flavor Synthesis, I. Menthol Esters of Varying Size and Polarity", J. Polym. Sci., Polym. Chem. Ed., 18(10), pp. 2933-2940 (1990).

Chemical Abstract Service, Abstract No. 88:11744p (1978).

Chemical Abstract Service, Abstract No. 103(2):11234a.

Chemical Abstract Service, Abstract No. 107(8):64668j.

Chemical Abstract Service, Abstract No. 108(2):11014g.

Chemical Abstract Service, Abstract No. 110(16):141301a.

Chemical Abstract Service, Abstract No. 110(18):160412d.

Gennaro. (1985). Remington's Pharmaceutical Sciences, Mack Pub., p. 792.

*Primary Examiner*—Thurman K. Page
*Assistant Examiner*—Raj Bawa
*Attorney, Agent, or Firm*—Kim William Zerby; Douglas C. Mohl; Richard C. Witte

[57] ABSTRACT

Ingestible pharmaceutical compositions comprising pharmaceutical actives useful for treating upper gastrointestinal tract distress (e.g., antacid agents) and 3-1-menthoxy propane 1,2-diol in amounts effective for providing a cooling sensation to the throat.

18 Claims, No Drawings

INGESTIBLE PHARMACEUTICAL COMPOSITIONS FOR TREATING UPPER GASTROINTESTINAL TRACT DISTRESS

This is a continuation of application Ser. No. 680,459 filed Apr. 4, 1991, now abandoned.

BACKGROUND OF THE INVENTION

The present invention relates to ingestible pharmaceutical compositions comprising pharmaceutical actives useful for treating upper gastrointestinal tract distress and 3-1-menthoxy propane 1,2-diol ("MPD") in amounts effective for providing a cooling sensation in the throat.

Pharmaceutical compositions, such as antacids, useful for treating upper gastrointestinal tract distress (such as heartburn, indigestion, stomachache, etc.) are widely used. They vary depending on the active ingredients, and increasingly differ in the flavors, texture and even forms. The excipients for such compositions are chosen not only as appropriate for the dose form, but also to provide the best possible aesthetics for the compositions, including texture, flavor, after-taste, etc. Depending on the active used, and to some extent the excipients utilized, the time for the therapeutic effect of the active ingredient to be meaningful to the consumer will vary. Frequently, however, the time when the consumer actually begins to receive the benefit of the active ingredient and the time when the consumer perceives the product as starting to "work" are different. Dose form, flavorants, texture, etc. probably all contribute at least in part to this perception. Obviously, for the consumer in need of relief for upper gastrointestinal tract distress, perceiving that the product is working as quickly as possible after ingestion is of great benefit in addition to the true therapeutic relief eventually provided by the active ingredient.

In spite of the large amount of research directed to providing faster acting compositions for treating upper gastrointestinal distress, there continues to be a need for compositions which not only do act faster but also which are perceived by consumers as working faster. Surprisingly, it has been discovered that including the coolant MPD (which is very effective for providing a cooling sensation to the throat) results in the perception by the consumer that the pharmaceutical composition is working. Thus, while this coolant has no apparent therapeutic activity, the signal it provides to the consumer in need of fast relief of upper gastrointestinal distress is of great benefit for the perception that relief is already being provided. Even more surprising is that this improved signal of relief is recognized when compositions according to the present invention are compared against similar compositions containing menthol (which has a noticeably different cooling profile from MPD).

Thus, it is an object of the present invention to provide ingestible pharmaceutical compositions containing a pharmaceutical active useful for treating upper gastrointestinal tract distress (e.g., upset stomach, heartburn, indigestion) which are perceived as providing faster relief and/or greater perceived efficacy and/or longer duration of activity. Furthermore, an object is to provide methods for treating upper gastrointestinal distress by administering pharmaceutical compositions according to the present invention.

These and other objects of the present invention will become readily apparent from the detailed description which follows.

All percentages and ratios used herein are by weight, and all measurements are made at 25° C., unless otherwise specified.

SUMMARY OF THE INVENTION

The present invention is directed to ingestible pharmaceutical compositions comprising: (a) a safe and effective amount of a pharmaceutical active useful for treating upper gastrointestinal tract distress; and (b) at least one excipient comprising an amount of 3-1-menthoxy propane 1,2-diol effective for providing a cooling sensation to the throat.

The present invention is also directed to methods for treating upper gastrointestinal tract distress. These methods comprise orally administering to a human patient in need of such treatment a safe and effective amount of a pharmaceutical active useful for treating upper gastrointestinal tract distress and an amount of 3-1-menthoxy propane 1,2-diol effective for providing a cooling sensation to the throat.

DETAILED DESCRIPTION OF THE INVENTION

The present invention relates to pharmaceutical compositions comprising: (a) at least one pharmaceutical active useful for treating upper gastrointestinal tract distress (preferably antacid actives); and (b) at least one excipient comprising 3-1-menthoxy propane 1,2-diol (hereinafter "MPD") effective for providing a cooling sensation to the throat.

Pharmaceutical actives useful for treating upper gastrointestinal tract distress are those materials which are safe and effective when administered orally for treating disorders of the upper gastrointestinal tract (typically the stomach and/or esophagus) which result in symptoms of upper gastrointestinal tract distress (e.g., heartburn, stomachache, indigestion). Such actives include antacid agents and acid secretion prevention agents (e.g., $H_2$ receptor-blocking antisecretory agents). Antacid agents include, for example, aluminum carbonate, aluminum hydroxide, aluminum phosphate, aluminum hydroxy-carbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilicate, sucralfate, and mixtures thereof. Examples of acid secretion prevention agents include cimetidine, ranitidine, famotidine, omeprazole, and mixtures thereof. Other useful pharmaceutical actives include bismuth-containing agents such as, for example, bismuth subsalicylate, bismuth aluminate, bismuth citrate, bismuth subcitrate, bismuth nitrate, bismuth subcarbonate, bismuth subgalate, and mixtures thereof. A particularly preferred bismuth salt is bismuth subsalicylate.

Preferred for use herein are antacid agents. Preferred antacid agents are aluminum hydroxide, magnesium hydroxide, dihydroxy aluminum sodium carbonate, calcium carbonate, and mixtures thereof. Most preferred is calcium carbonate.

The compositions of the present invention comprise a safe and effective amount of at least one pharmaceutical active useful for treating upper gastrointestinal tract distress. Typically the pharmaceutical active(s) comprise from about 1% to about 99%, by weight, of the pharmaceutical compositions of the present invention, preferably from about 25% to about 60%, and most preferably from about 30% to about 50%.

The pharmaceutical compositions of the present invention also comprise an amount of MPD effective for providing a cooling sensation to the throat. This material is described in detail in U.S. Pat. No. 4,459,425, issued Jul. 10, 1984 to Amano et al., incorporated herein by reference in its entirety. While not to be limited by theory, it is believed that the surprising benefits obtained by the use of MPD in the compositions of the present invention are the result of the unique cooling profile for this compound, which is very noticeable in the throat. MPD is commercially available, being sold by Takasago Perfumery Co., Ltd., Tokyo, Japan.

In addition, excipients other than the MPD may optionally be included in the present compositions. The term "excipients", as used herein, means one or more compatible solid or liquid filler diluents or encapsulating substances which are suitable for oral administration to a human. The term "compatible", as used herein, means that the components of the compositions of the present invention are capable of being commingled with the pharmaceutical active, and with each other, in a manner such that there is no interaction which would substantially reduce the pharmaceutical efficacy of the compositions under ordinary use situations. Excipients must, of course, be of sufficiently high purity and sufficiently low toxicity to render them suitable for administration to the human being treated.

Some examples of substances which can serve as excipients in addition to the MPD are sugars such as lactose, glucose and sucrose; starches such as cornstarch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; and alginic acid; as well as other non-toxic compatible substances used in pharmaceutical formulations. Wetting agents and lubricants such as sodium lauryl sulfate, as well as coloring agents, flavoring agents, sweetening agents (including nonnutritive sweeteners such as aspartame and saccharin), tableting agents, stabilizers, antioxidants, cooling agents, and preservatives, can also be present. Other compatible pharmaceutical additives and actives which are not pharmaceutical actives useful for treating upper gastrointestinal tract distress (e.g., NSAI drugs; pain killers; muscle relaxants) may be included in the compositions of the present invention. Also, it is to be noted that in addition to the MPD, other materials having cooling properties may optionally be included within the excipients, such as menthol, menthol-like compounds such as N-ethyl-p-menthane-3-carboxamide ("WS-3", supplied by Sterling Drugs), and mixtures thereof.

The choice of excipients to be used in conjunction with the pharmaceutical active of the present compositions is basically determined by the dose form for the compositions. The preferred dosage forms are liquid solutions, liquid suspensions, tablets, especially chewable tablets, capsules and the like, comprising a safe and effective amount of the pharmaceutical actives. Excipients suitable for the preparation of dosage forms for oral administration are well-known in the art. Their selection will depend on secondary considerations like taste, cost, shelf stability, which are not critical for the purposes of the present invention, and can be made without difficulty by a person skilled in the art.

The excipients employed in the present ingestible compositions are used at concentrations sufficient to provide a practical size to dosage relationship. Typically, excipients comprise from about 1% to about 99% by weight of the pharmaceutical compositions of the present invention, preferably from about 40% to about 75%, and most preferably from about 50% to about 70%. Additionally, the MPD typically comprises from about 0.01% to about 0.50% by weight of the pharmaceutical compositions of the present invention, preferably from about 0.02% to about 0.20%, and most preferably from about 0.04% to about 0.10%.

The present invention also relates to methods for treating upper gastrointestinal tract distress in humans. These methods comprise orally administering to a human in need of such treatment a safe and effective amount of a pharmaceutical active useful for treating upper gastrointestinal tract distress and an amount of MPD effective for providing a cooling sensation to the throat. Most preferred is administering a safe and effective amount of an ingestible pharmaceutical composition of the present invention.

The following examples further describe and demonstrate embodiments within the scope of the present invention. These examples are given solely for the purpose of illustration and are not to be construed as a limitation of the present invention as many variations thereof are possible without departing from the spirit and scope.

EXAMPLE I

An ingestible pharmaceutical composition according to the present invention in the form of a chewable antacid tablet is prepared as follows:

| Ingredients | Weight % |
| --- | --- |
| Granulated calcium carbonate[1] | 42.87% |
| Magnesium stearate | 2.50% |
| Colored speckles | 0.75% |
| Flavorants | 0.78% |
| MPD[2] | 0.07% |
| WS-3[3] | 0.05% |
| Aspartame | 0.198% |
| Sodium Saccharin | 0.102% |
| Mannitol[4] | Q.S. |

[1] Granulated calcium carbonate containing 93.3% calcium carbonate, 6.3% glucose and 0.4% gelatin; supplied by Whittaker Clark & Daniels, Philadelphia, Pa.
[2] 3-l-menthoxy propane 1,2-diol, supplied by Takasago Perfumery Co., Ltd., Tokyo, Japan.
[3] N-ethyl-p-menthane-3-carboxamide, supplied by Sterling Drugs.
[4] Granulate mannitol supplied by ICI Americas, Inc., Wilmington, Delaware.

The above ingredients are dry blended in a mixer until homogeneous, and then direct compressed in a tabletting machine to approximately 8.5 Strong Cobb units hardness to produce chewable antacid tablets each weighing 1.25 g (500 mg calcium carbonate per tablet).

Ingestion of one or two of these tablets by a human subject suffering from heartburn, acid indigestion and upset stomach associated with these symptoms provides effective relief for this upper gastrointestinal tract distress.

What is claimed is:

1. Ingestible pharmaceutical compositions comprising:
   (a) from about 1% to about 99% of at least one pharmaceutical active useful for treating upper gastrointestinal tract distress selected from the group consisting of antacid agents, acid secretion prevention agents, bismuth-containing agents, and mixtures thereof; and
   (b) from about 1% to about 99% of at least one excipient comprising 3-1-menthoxy propane 1,2-diol.

2. Ingestible pharmaceutical compositions according to claim 1 wherein the pharmaceutical active is selected from the group consisting of aluminum carbonate, aluminum hydroxide, aluminum phosphate, aluminum hydroxy-carbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilicate, sucralfate, cimetidine, ranitidine, famotidine, omeprazole, bismuth subsalicylate, bismuth aluminate, bismuth citrate, bismuth subcitrate, bismuth nitrate, bismuth subcarbonate, bismuth subgalate, and mixtures thereof.

3. Ingestible pharmaceutical compositions according to claim 2 wherein the excipient further comprises one or more excipients selected from the group consisting of wetting agents, lubricants, tableting agents, flavoring agents, sweetening agents, coloring agents, stabilizers, antioxidants, cooling agents, preservatives, and mixtures thereof.

4. Ingestible pharmaceutical compositions according to claim 3 wherein the excipients comprise at least one cooling agent selected from menthol, menthol-like compounds, and mixtures thereof.

5. Compositions according to claim 4 wherein the cooling agent comprises N-ethyl-p-menthane-3-carboxamide.

6. Ingestible pharmaceutical compositions comprising:
   (a) from about 25% to about 60% of at least one pharmaceutical agent useful for treating upper gastrointestinal tract distress selected from the group consisting of aluminum carbonate, aluminum hydroxide, aluminum phosphate, aluminum hydroxy-carbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilicate, sucralfate, cimetidine, ranitidine, famotidine, omeprazole, bismuth subsalicylate, bismuth aluminate, bismuth citrate, bismuth subcitrate, bismuth nitrate, bismuth subcarbonate, bismuth subgalate, and mixtures thereof;
   (b) from about 40% to about 75% of excipients comprising 3-1-menthoxy propane 1,2-diol and at least one other excipient selected from the group consisting of wetting agents, lubricants, coloring agents, flavoring agent, sweetening agents, tableting agents, stabilizers, antioxidants, cooling agents, preservatives, and mixtures thereof.

7. Ingestible pharmaceutical compositions according to claim 6 wherein the pharmaceutical active is selected from the group consisting of aluminum carbonate, aluminum hydroxide, aluminum phosphate, aluminum hydroxy-carbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilicate, sucralfate, and mixtures thereof, and wherein further the 3-1-menthoxy propane 1,2-diol comprises from about 0.01% to about 0.50% by weight of the composition.

8. Ingestible pharmaceutical compositions according to claim 7 wherein the pharmaceutical active comprises from about 1% to about 99% calcium carbonate.

9. Ingestible pharmaceutical compositions according to claim 8 wherein the 3-1-menthoxy propane 1,2-diol comprises from about 0.02% to about 0.20% by weight of the composition.

10. Ingestible pharmaceutical compositions according to claim 9 wherein the excipients further comprise at least one cooling agent selected from menthol, N-ethyl-p-menthane-3-carboxamide, and mixtures thereof.

11. Ingestible pharmaceutical compositions according to claim 10 in unit dose form.

12. A method for treating upper gastrointestinal tract distress in humans, said method comprises orally administering to a human patient in need of such treatment a composition according to claim 1 in an amount safe for human oral consumption and effective for treating said upper gastrointestinal tract distress.

13. A method for treating upper gastrointestinal tract distress in humans, said method comprises orally administering to a human patient in need of such treatment a composition according to claim 2 in an amount safe for human oral consumption and effective for treating said upper gastrointestinal tract distress.

14. A method for treating upper gastrointestinal tract distress in humans, said method comprises orally administering to a human patient in need of such treatment a composition according to claim 5 in an amount safe for human oral consumption and effective for treating said upper gastrointestinal tract distress.

15. A method for treating upper gastrointestinal tract distress in humans, said method comprises orally administering to a human patient in need of such treatment a composition according to claim 6 in an amount safe for human oral consumption and effective for treating said upper gastrointestinal tract distress.

16. A method for treating upper gastrointestinal tract distress in humans, said method comprises orally administering to a human patient in need of such treatment a composition according to claim 7 in an amount safe for human oral consumption and effective for treating said upper gastrointestinal tract distress.

17. A method for treating upper gastrointestinal tract distress in humans, said method comprises orally administering to a human patient in need of such treatment a composition according to claim 8 in an amount safe for human oral consumption and effective for treating said upper gastrointestinal tract distress.

18. A method for treating upper gastrointestinal tract distress in humans, said method comprises orally administering to a human patient in need of such treatment a composition according to claim 9 in an amount safe for human oral consumption and effective for treating said upper gastrointestinal tract distress.

* * * * *